(12) United States Patent
Hagege

(10) Patent No.: US 8,634,920 B2
(45) Date of Patent: Jan. 21, 2014

(54) DEVICE FOR PERINEUM REEDUCATION

(75) Inventor: Edward Hagege, Naharya (IL)

(73) Assignee: Perinealis Ltd., Nicosia (CY)

( * ) Notice: Subject to any disclaimer, the term of this patent is extended or adjusted under 35 U.S.C. 154(b) by 153 days.

(21) Appl. No.: 13/063,949

(22) PCT Filed: Sep. 14, 2009

(86) PCT No.: PCT/FR2009/051722
§ 371 (c)(1),
(2), (4) Date: May 6, 2011

(87) PCT Pub. No.: WO2010/031950
PCT Pub. Date: Mar. 25, 2010

(65) Prior Publication Data
US 2011/0230931 A1    Sep. 22, 2011

(30) Foreign Application Priority Data

Sep. 16, 2008 (FR) ..................................... 08 56231

(51) Int. Cl.
*A61N 1/00* (2006.01)
(52) U.S. Cl.
USPC .......................................................... 607/41
(58) Field of Classification Search
USPC .................................................. 607/39–41
See application file for complete search history.

(56) References Cited

U.S. PATENT DOCUMENTS

| 4,205,671 | A  | * | 6/1980  | Lassen .......................... 128/886 |
| 5,702,428 | A  |   | 12/1997 | Tippey et al. |
| 2006/0190049 | A1 | * | 8/2006 | Gerber et al. .................... 607/41 |
| 2007/0066995 | A1 | * | 3/2007 | Strother et al. ................... 607/2 |
| 2007/0260288 | A1 | * | 11/2007 | Gross .............................. 607/41 |

FOREIGN PATENT DOCUMENTS

| GB | 2 435 834 | 9/2007 |
| WO | 01/60446 | 8/2001 |
| WO | 2007/059989 | 5/2007 |

* cited by examiner

*Primary Examiner* — Scott Getzow
(74) *Attorney, Agent, or Firm* — Clark & Brody

(57) ABSTRACT

The invention provides a perineal rehabilitation device comprising an applicator that is either an endocavity applicator (100) or an annular applicator (100'), locally supporting a charging electrode (104, 105) and at least one stimulation electrode (101, 102) respectively on its periphery or on its inside face, and including at least one energy storage unit that is rechargeable via the charging applicator (104, 105), the applicator (100, 100') including at least one microprocessor for executing an electrical stimulation program, the device being characterized in that the applicator (100, 100') is controlled by a control module (200) in the form of a remote control connected to the applicator (100, 100') by a wireless connection and including a user interface for enabling the user to input operating data for the applicator (100, 100') and a control unit for controlling the applicator (100, 100') by sending control signals thereto, the applicator (100, 100') being suitable for receiving control signals for modifying the intensity of stimulation while it is in operation and for modifying its ongoing operation as a function of such control signals.

11 Claims, 6 Drawing Sheets

DEVICE FOR PERINEUM REEDUCATION

BACKGROUND OF THE INVENTION

The present invention relates to the general field of perineal rehabilitation devices.

More particularly, the present invention relates to perineal rehabilitation devices comprising an endocavity or an annular applicator or probe locally supporting a charging electrode and at least one stimulation electrode either on its periphery or in its inside face, said applicator including at least one energy storage unit that is rechargeable via the charging electrode.

Such a probe or applicator is used, amongst other possibilities, in particular for treating urinary incontinence. Urinary incontinence is manifested by an involuntary loss of urine that many people find problematic.

There are two main types of urinary incontinence, stress incontinence and urgent incontinence.

Stress incontinence corresponds to loss of urine as a result of an increase in abdominal pressure on the bladder. This increase in pressure may be due to coughing, sneezing, laughing, or making a movement, in particular lifting something heavy. Stress incontinence is the most common type of incontinence and it mainly affects women. It takes place in general when the perineal muscles and the muscles of the floor of the pelvis are weakened, e.g. by pregnancies, childbirth, or the menopause.

Urgent incontinence corresponds to a sudden and pressing need to urinate, followed by an immediate contraction of the bladder. This contraction results in an involuntary loss of urine. Both men and women may be affected by this type of incontinence, in particular among older people. One of the reasons for such incontinence is a failure in the operation of the nervous system controlling the bladder.

Mixed incontinence is a combination of stress incontinence and of urgent incontinence.

In order to treat incontinence, it is known to make use of electrical stimulation, e.g. using a vaginal applicator, or in certain circumstances using surface electrodes. The use of such electrical stimulation is treatment that is well tolerated and that has demonstrated good results in improving control over the bladder and the intestines.

Thus, electrical stimulation via the pelvic nerves is a recognized treatment alternative for urinary incontinence. This treatment is also proposed in order to solve fecal incontinence due to dysfunction of the floor of the pelvis.

When treating stress incontinence, the purpose of electrical stimulation is to stimulate voluntary muscular contraction and to improve the working of the muscles of the floor of the pelvis. For urgent incontinence, the purpose is to inhibit involuntary contractions of the bladder by stimulating the nerves of the floor of the pelvis. When treating mixed incontinence, particular stimulation is used that is appropriate both for urgent incontinence and for stress incontinence.

At present, devices exist that are suitable for generating electrical stimulation for treating incontinence. Some such appliances are based on using a control platform connected by a wire to an endocavity applicator carrying stimulation electrodes, or indeed stimulation electrodes that are placed outside on the skin. Such appliances are used in the offices of physiotherapists or other health professionals. Such devices are not portable in any way.

Such wired devices used by physiotherapists make many parameter modifications available. It is not possible to envisage the general public using such devices without the presence of a health professional. Such prior art devices therefore cannot be used individually at any location and in particular at a user's home. Such wired appliances are also very expensive and require special training for their use.

There also exists a wireless perineal electrical stimulator that is rechargeable in a non-leaktight charger box. The charger box is also used for programming the applicator.

With that device, the applicator, or probe, is programmed using the charger box while the probe is still installed therein. Once the applicator is disconnected from the charger, it is no longer possible to modify is operation. Thus, once the applicator is programmed, it is designed to remain inactive for three minutes, thereby giving the user time to insert the applicator.

The device then runs the selected program. Such automatic activation of the applicator after three minutes of inactivity presents a certain number of problems, or even dangers. In particular, if the applicator is not inserted within three minutes following its disconnection, but is inserted later, the user runs the risk of electrocution since the program is already running.

Furthermore, the user has no access to electrical stimulation time ranges other than by means of the user's own sensations. Unfortunately, it is known that useful electrical stimulation is not necessarily perceived. Consequently, muscle contraction exercises cannot be performed thoroughly and reliably during electrical stimulation.

Thus, blind operation of known portable devices presents the advantage of enabling them to be used by the general public and without prior knowledge. However their operation is not without risk and does not enable treatment to be optimized.

OBJECT AND SUMMARY OF THE INVENTION

A main object of the present invention is thus to mitigate the drawbacks of the prior art by proposing a perineal rehabilitation device comprising an applicator that is either an endocavity applicator or an annular applicator, locally supporting a charging electrode and at least one stimulation electrode respectively on its periphery or on its inside face, and including at least one energy storage unit that is rechargeable via the charging applicator, the applicator including at least one microprocessor for executing an electrical stimulation program, the device being characterized in that the applicator is controlled by a control module in the form of a remote control connected to the applicator by a wireless connection and including a user interface for enabling the user to input operating data for the applicator and a control unit for controlling the applicator by sending control signals thereto, the applicator being suitable for receiving control signals for modifying the intensity of stimulation while it is in operation and for modifying its ongoing operation as a function of such control signals.

Such a perineal rehabilitation device comprises not only the applicator but also a control module enabling the intensity of stimulation to be modified while the applicator is in operation, thereby limiting any risk of electrocuting the user. The perineal rehabilitation device of the invention enables the applicator to begin operating at zero intensity, regardless of which electrical stimulation program was selected previously.

With the invention, it is possible to make provision for all of the electrical stimulation programs to begin at zero intensity. The intensity is modified solely by the user taking action on the remote control. The use of wireless communication between the control module and the applicator is a characteristic that is essential for implementing intensity modification of the stimulation.

The use of such a wireless connection is never mentioned in prior art devices. In prior art devices, the applicator is programmed while it is in place in the charger device. Thus, in prior art devices, program selection is performed by communication with contact between the applicator and the charger device.

The use of wireless communication between the control module and the applicator is an original characteristic of the invention. The fact that the control module specifically enables the intensity of stimulation to be modified remotely solves a particular problem in the use of a wireless applicator for a perineal rehabilitation device. The invention relates specifically to such remote modification of the intensity of stimulation.

With wired devices, the problem of electric shocks does not arise in the same way. Firstly, known wired devices are designed to be handled by personnel having training concerning electrical risks. Furthermore, the structure of those devices, based on the use of multiple electrodes, guarantees grounding, so there is no risk of the patient being electrocuted.

The particular intensity modification that is provided in original manner by the invention using the control module thus solves a particular problem that is encountered only with wireless probes.

Thus, and advantageously, all of the programs begin electrical stimulation at zero intensity.

This characteristic should be understood as meaning that programs begin at low intensity such that there is no possibility of electrocuting the user. It is not absolutely essential for the starting intensity to be strictly zero.

According to an advantageous characteristic, the control module includes means for indicating stimulation operating ranges of the applicator.

This characteristic enables the user to know when the applicator is emitting electrical stimuli. This enables the user to contract muscles at the same time, thus optimizing treatment by performing exercises known as Kegel exercises. This characteristic may be implemented insofar as the device has an external remote control connected to the probe or applicator via wireless communication, and in particular when the connection is bidirectional, thus enabling the probe to return information about its stimulation operating ranges. In other words, the control of the control module over the probe of the invention can also enable this characteristic to be implemented.

According to a particular characteristic of the invention, the control module includes a memory for storing time-stamped data concerning the operating intensities and durations requested of the applicator.

In variant embodiments, it is also possible for the applicator to include a memory.

The presence of such a memory makes it possible to store data about the treatment ranges used by the user. In particular, such a memory may be read by means of dedicated software installed on a doctor's computer. Reading this memory informs the doctor about all of the treatment ranges used by the patient, and also about their characteristics.

Thus, according to a particular characteristic of the invention, the control module includes at least one connection port for transferring time-stamp data to a computer.

According to a particular characteristic of the invention, the control module includes means suitable for sending control signals to the applicator, either automatically or on user input, causing the applicator to issue stimuli of increasing intensity, and the interface includes means enabling the user to indicate the moment when the stimuli begin to be felt.

Advantageously, the intensity used when the user indicates that the stimulation can be felt is stored within the control module.

In particular when it is implemented at the beginning of treatment, this characteristic makes it possible to know the user's sensitivity to the stimuli. Such data is useful in enabling the doctor to evaluate how treatment is progressing.

This characteristic increases the intensity of the stimuli progressively, starting from a stimulus of zero intensity. This operating protocol makes it possible to ensure that the patient does not suffer any electric shock.

The increase in the intensity of the stimuli may take place automatically or it may be controlled by the patient using buttons placed on the interface of the control module. When the increase in intensity is controlled by the user, the device is particularly reliable from the point of view of absence of risk of electrocution.

According to another particular characteristic of the invention, the applicator, while in operation, is suitable for taking measurements relating to the reaction of the body.

The use of the applicator for taking measurements relating to the reaction of the body provides feedback concerning the user's reaction to the treatment. These measurements may be taken by means of electrodes, or alternatively, according to an advantageous characteristic, by using a pressure sensor implemented on the applicator to take measurements relating to the reaction of the body.

In particular, such a pressure sensor makes it possible to measure the reaction of the muscle during electrical stimulation, in particular to measure its contraction. The magnitude of the reaction of the muscle to the stimuli enables the changes in user training to be tracked. This makes it possible to give information about changes to the anatomical structures involved.

By way of example, the measurements relating to the reaction of the body may be stored in a memory of the applicator.

According to an advantageous characteristic, these measurements may also be returned to the control module, providing the wireless connection is bidirectional.

Thus, when the wireless connection is bidirectional, according to a particular characteristic of the invention, the control module includes a "feedback" unit for receiving measurements from the applicator, for processing these measurements in real time, for calculating an appropriate operating mode as a function of the measurements, and for sending a control signal corresponding to this mode of operation to the applicator.

With this characteristic, it is ensured that the applicator operates in a mode of operation that complies with the reaction of the user's body. In particular, this makes it possible to avoid strongly stimulating muscles that present a reaction that has diminished as a result of making repeated efforts, while nevertheless continuing to apply some stimulation. This amounts to providing the operation of the device with "biofeedback".

This particular characteristic makes it possible to provide an appliance for training that is physical, and not necessarily medical. This makes it possible to exercise muscles on fitness principles.

In addition, according to an advantageous characteristic, the control module includes the memory for storing the information relating to the reaction of the body.

Such a memory serves to keep track of the reactions of the patient's body and to provide fatigue curves for the muscle. These reactions of the body may be used for adjusting subsequent operation of the applicator or indeed for tracking variation in the muscle.

According to an advantageous characteristic of the invention, the applicator includes an electrode for detecting that it has been inserted or installed correctly, which electrode is suitable for detecting contact with the body, said electrode being suitable for sending a signal to the microprocessor installed within the applicator and/or the microprocessor installed within the control module, the microprocessor being such as to be suitable for causing stimulation to stop as soon as the applicator is no longer in contact with the body.

This characteristic enables stimulation to be stopped as soon as the applicator is no longer in place.

The invention also provides an endocavity applicator locally supporting at least one charging electrode, and, at its periphery, at least one stimulation electrode, and at least one energy storage unit that is rechargeable via the charging electrode, the applicator being for use with a control module connected to the applicator by a wireless communication connection for forming a perineal rehabilitation device of the invention.

The invention also provides an annular applicator locally supporting at least one charging electrode, and, at its inside face, at least one stimulation electrode, and at least one energy storage unit that is rechargeable via the charging electrode, the applicator being for use with a control module connected to the applicator by a wireless communication connection for forming a perineal rehabilitation device of the invention.

The invention also provides a control module connected to an endocavity or an annular applicator of the invention via a wireless communication connection and including a user interface to enable the user to input operating data for the applicator, and a control unit for controlling the applicator by sending intensity-modifying control signals thereto.

Finally, the invention provides a method of controlling an endocavity or an annular applicator, which method is implemented in a perineal rehabilitation device of the invention and comprises the following steps for the control module:

receiving applicator operation data input by the user and relating to the intensity of stimulation; and sending control signals for modifying the intensity of stimulation to the applicator;

and comprises the following steps for the applicator while in operation:

receiving control signals sent by the control module; and modifying the ongoing operation.

According to an advantageous characteristic of the invention, the method includes the following initialization steps:

for the control module, sending control signals to the applicator causing it to issue stimuli of increasing intensity, either automatically or under user control;

for the applicator, receiving control signals and issuing successive stimuli of increasing intensity;

for the control module, receiving from the interface actuated by the user a signal marking the moment at which the stimuli begins to be felt; and for the control module, storing the intensity then in use, representing the minimum intensity threshold felt by the user.

According to a particular characteristic of the invention, the method includes the following feedback steps:

for the applicator, using the electrodes while it is in operation to take measurements relating to the reaction of the user's body;

for the control module, receiving measurements from the applicator;

processing the measurements in real time;

calculating an operating mode that is adapted as a function of the measurements; and sending a control signal corresponding to said mode of operation to the applicator; and for the applicator, modifying its ongoing operation in accordance with the control signal.

In a preferred implementation, the various steps of the method are determined by computer program instructions.

Consequently, the invention also provides a computer program including instructions for executing steps of the method of the invention for controlling an endocavity or an annular applicator when said program is executed by a microprocessor computer.

The program may use any programming language, and it may be in the form of source code, object code, or code intermediate between source code and object code, such as in a partially compiled form, or in any other desirable form.

The invention also provides a storage medium readable by a computer and having a computer program stored thereon including instructions for executing steps of the method of the invention for controlling an endocavity or annular applicator.

The data medium may be any kind of entity or device capable of storing the program. For example, the medium may include storage means such as a read-only memory (ROM), e.g. a compact disk (CD) or a micro-electronic circuit ROM, or indeed magnetic storage means, e.g. a floppy disk, a hard disk, a flash memory, etc.

Furthermore, the data medium may be a transmission medium such as an electrical or an optical signal suitable for being conveyed via an electrical or optical cable, by radio, or by other means. The program of the invention may in particular be downloaded from a network of the Internet type.

Alternatively, the data medium may be an integrated circuit in which the program is incorporated, the circuit being adapted to execute or to be used in the execution of the method in question.

BRIEF DESCRIPTION OF THE DRAWINGS

Other characteristics and advantages of the present invention appear from the following description made with reference to the accompanying drawings that show an embodiment having no limiting character. In the figures.

DETAILED DESCRIPTION OF AN EMBODIMENT

Figure 1A:
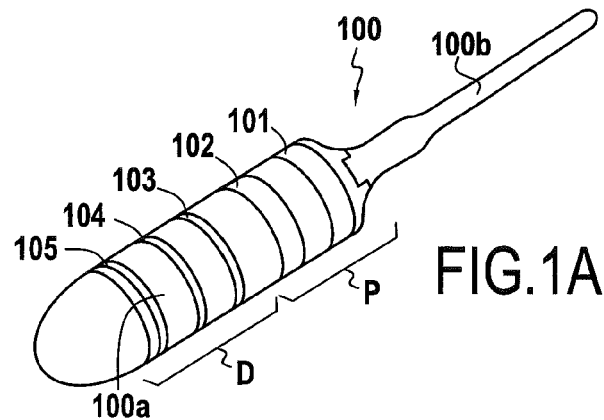
FIG. 1 shows an embodiment of a perineal rehabilitation device of the invention.

FIG. 1 shows a perineal rehabilitation device of the invention. FIG. 1A shows an endocavity applicator 100 comprising an oblong portion 100a for inserting into the cavity, e.g. the vagina, and a long thin portion 100b constituting a handle for removing the applicator after it has been inserted. The endocavity applicator is advantageously leaktight so as to be easy to clean.

The oblong portion 100a is provided with annular electrodes, here five electrodes 101 to 105. Other electrode shapes, in particular as circular arcs could possibly be implemented.

It should be observed at this point that any type of wireless connection protocol may be used: preferably Bluetooth or radiofrequency (RF), but various other protocols could also be envisaged.

The distal portion referenced D of the oblong portion 100a is provided with at least two electrodes 104 and 105 used for charging the applicator 100. A third electrode 103 is advantageously added to detect that the applicator 100 has been inserted in a body cavity, e.g. the vagina. This avoids electric shocks.

The role of this detector electrode 103 is to provide a signal to a microprocessor that manages stimulation within the applicator 100 so that the stimulation does not start or is stopped when the applicator 100 is outside the body or when the applicator 100 is extracted from the vagina. In addition to this sensor, the applicator is also advantageously such that the electric current or intensity on all of its channels can be reduced to zero at any moment so as to be in a position to remove the applicator at any moment.

The proximal portion referenced P of the oblong portion 100a is provided with at least two stimulation electrodes 101 and 102 to which sequences of electrical stimuli are applied.

It should be observed at this point that the number of stimulation electrodes could be greater. Nevertheless, studies have shown that the ratio of the number of electrodes to the effectiveness of stimuli is very satisfactory when using two electrodes. The stimulation electrodes occupy the first four centimeters of the proximal portion P of the oblong portion 100b. For vaginal use, it is in this location that the stimulation is found to be the most effective, it being understood that the device is designed for the applicator 100 to be inserted in such a manner that the oblong portion 100a is inserted in full.

The applicator 100 includes at least one microprocessor for implementing the stimuli and for managing them within the wirelessly-connected probe-applicator.

Figure 1B:
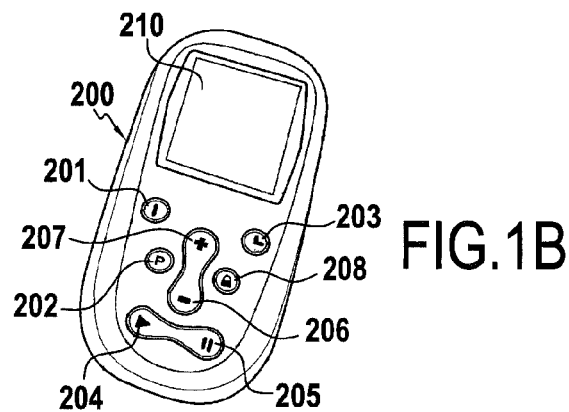

FIG. 1B shows a control module 200 in the form of a remote control of the invention. In the embodiment shown, the module 200 has a display screen 210 and a certain number of control buttons, here eight buttons referenced 201 to 208 and acting as an interface for the user.

The control module 200 also includes a battery that makes it independent, at least one microprocessor, and units that are implemented in hardware or software.

It thus comprises an applicator control unit for determining and sending control signals to the applicator, and at least one memory for storing operating data concerning the applicator.

A button 201 serves to switch the device on and off. This button 201 is also used for stopping stimulation at any moment. A button 204 enables treatment to be started.

A button 203 serves to activate a window for programming the duration of treatment. Typically, a duration lying in the range 1 minute (min) to 45 min may be selected, by using the + and − buttons 206 and 207.

A button 202 serves to activate a window for selecting a stimulation program, e.g. from amongst seven programs numbered P1 to P7. The program is selected by using the + and − buttons 206 and 207.

A button 208 serves to confirm or cancel selection. Two presses on the button 208 serve advantageously to return to the menu that was previously selected on the screen.

A button 205 serves to pause stimulation at any moment. Pressing simultaneously on this button 205 and on the button 203 serves advantageously to cancel the current programming.

The buttons 206 and 207 are also used during operation of the applicator 100 in order to increase and decrease the intensity of stimulation in accordance with an essential and original characteristic of the invention.

As described below, at least some of the buttons of the control module 200, including the + and − buttons 206 and 207, may also be used for controlling a display of data stored in the control module 200 on a computer that is connected to the control module 200.

Figure 1C:
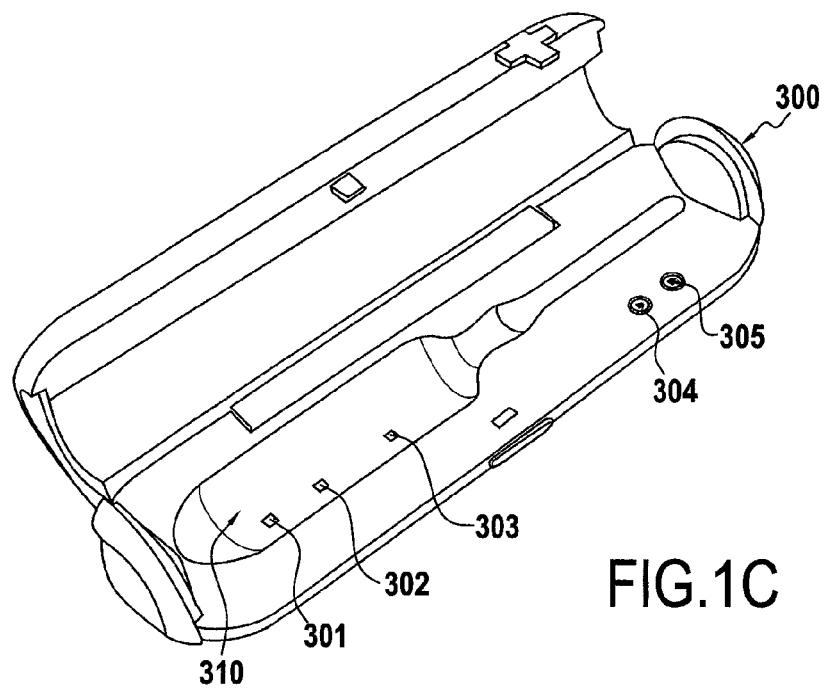

FIG. 1C shows a preferred implementation of a charger 300 used for an applicator 100 of the invention. The charger 300 is advantageously suitable for containing the applicator 100 for storage purposes. It contains a recess 310 having the same shape as the applicator 100. It presents contact electrodes 301 and 302 for charging the applicator 100 as soon as it is placed in the charger box 300. At least one third contact point 303 is used for monitoring the level of charge of the battery.

Indicator lights 304 and 305 serve to provide indication about the charging of the applicator 100.

Figure 2:
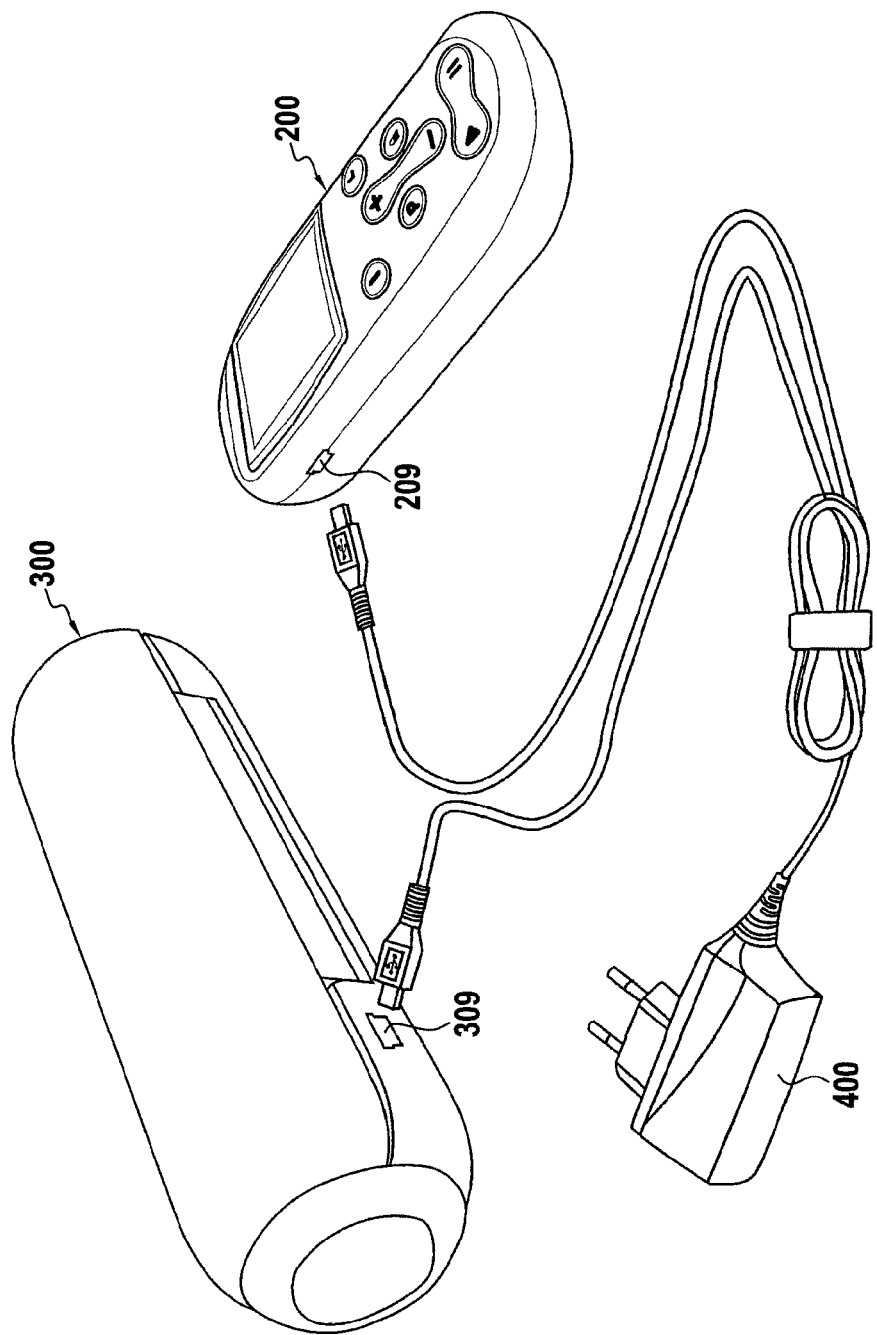
FIG. 2 shows a perineal rehabilitation device of the invention during a charging stage.

FIG. 2 shows the step of charging the applicator 100 inserted in the charger box 300 and of charging the control module 200. The charger box 300 and the control module 200 are advantageously provided with female universal serial bus (USB) connectors, preferably of small dimensions. These connectors are for connecting to mains via a charger transformer 400 and two cables, each provided with a male USB connector.

Figure 3:
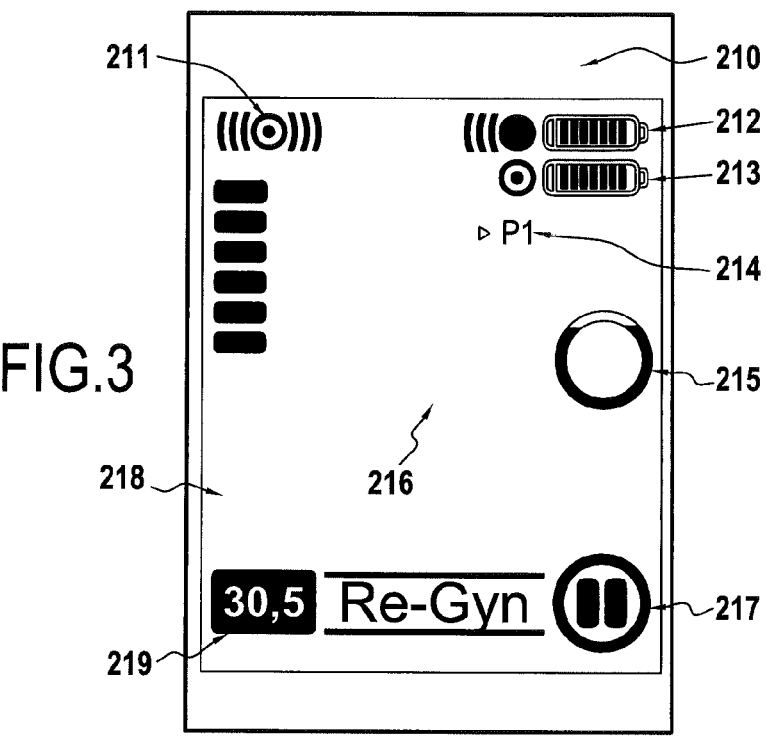
FIG. 3 shows an example of a display on the screen of the control module of the invention.

FIG. 3 shows an example of a display on the screen 210. A pictogram 211 indicates that the wireless connection with the applicator 100 is indeed established. A pictogram 212 indicates the level of charge of the battery of the control module 200. A pictogram 213 indicates the level of charge of the battery of the applicator 100.

A pictogram 214 specifies the program, in this example "P1", that is running or that has been selected. A pictogram 215 indicates that a stimulation operating range of the applicator is current. In this example, the pictogram 215 is constituted by a circle with a disk at its center that is lighted only when a stimulation is running.

A display zone 216 displays a timer showing the elapsed or remaining duration of the treatment. Where appropriate, a pictogram 217 appears when the applicator 100 is paused.

A graduated zone 218 displays the intensity of the current stimulation as a relative value. The display zone 219 gives the exact value of the intensity of the stimulation.

Figure 4:
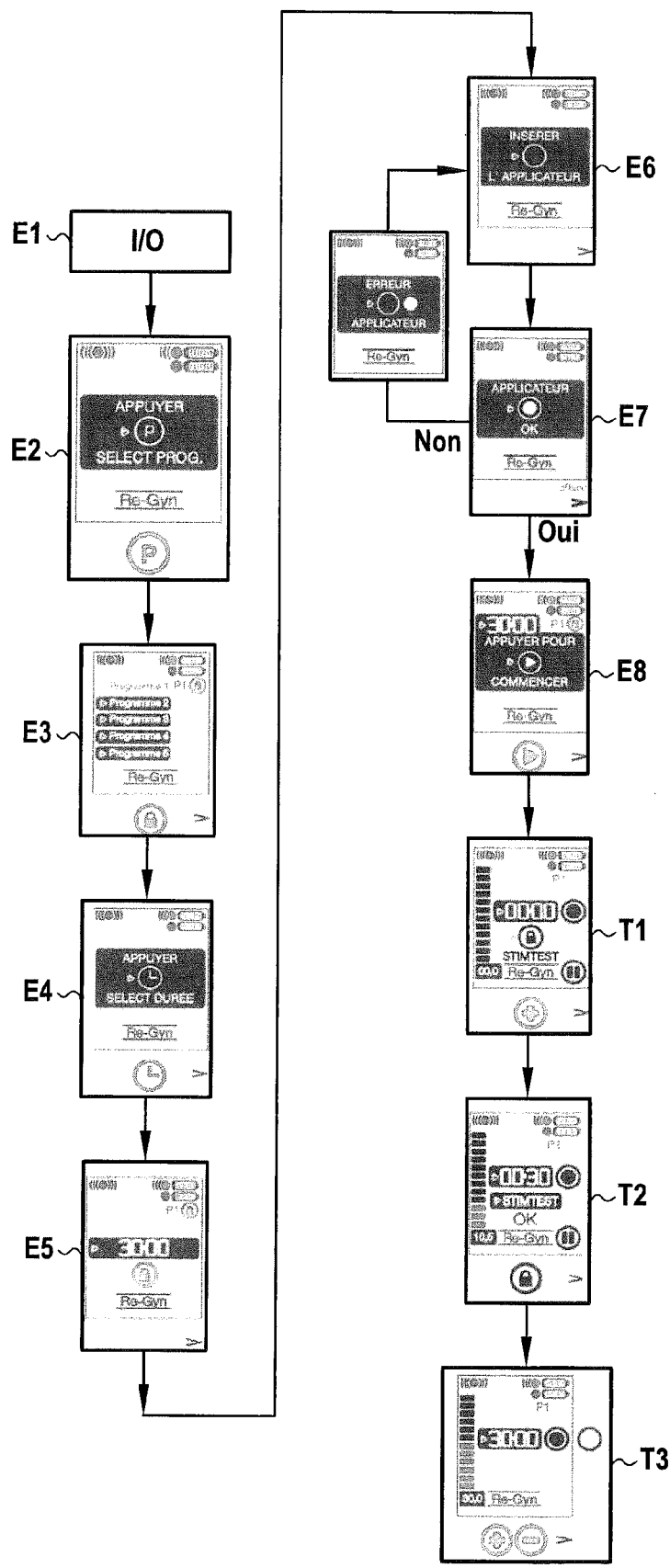
FIG. 4 is a flow chart showing the operation of the perineal rehabilitation device of the invention.

FIG. 4 is a flow chart showing the operation of the applicator 100 of the invention.

The control module 200 is switched on in a step E1 using the button 201. The screen 210 then invites the user to press on the button 202 in order to select a program Pi in a step E2.

Once the button 202 has been pressed, the user can select the program by using the buttons 206 and 207 to select from a list of programs. The user confirms a selection by pressing on the button 208 in a step E3.

Specifically, the user may select from among the following programs:

The first programs P1 to P3 are dedicated to treating stress incontinence.

| Pi | Frequency | Tpulse | Tstim | Trest | Recommended application |
|---|---|---|---|---|---|
| P1 | 50 hertz (Hz) | 200 microseconds (μs) | 3 seconds (s) | 6 s | 30 min, 3-5 times/week |
| P2 | 50 Hz | 200 μs | 5 s | 10 s | 30 min, 3-5 times/week |
| P3 | 50 Hz | 200 μs | 10 s | 20 s | 30 min, 3-5 times/week |

The following programs P4 to P6 are dedicated to treating mixed incontinence.

| Pi | Frequency | Tpulse | Tstim | Trest | Recommended application |
|---|---|---|---|---|---|
| P4 | 20 Hz | 200 μs | 3 s | 6 s | 30 min, 3-5 times/week |
| P5 | 20 Hz | 200 μs | 5 s | 10 s | 30 min, 3-5 times/week |
| P6 | 20 Hz | 200 μs | 10 s | 20 s | 30 min, 3-5 times/week |

Finally, the program P7 is dedicated to treating urgent incontinence.

| Pi | Frequency | Tpulse | Tstim | Trest | Recommended application |
|---|---|---|---|---|---|
| P7 | 10 Hz | 180 μs | Continuous | | 30 min, 2-5 times/week |

Thereafter, the screen invites the user to press the button 203 in order to select the duration of the treatment in a step E4. Once the duration has been selected using the buttons 206 and 207, the duration is confirmed using the button 208 in a step E5.

The screen 210 then invites the user to insert the applicator 100 in a step E6. The sensor 103 then serves to verify that the applicator 100 is indeed inserted before beginning the treatment in a step E7.

Advantageously, the wireless connection between the control module 200 and the applicator 100 is a bidirectional connection, and the signal issued by the sensor 103 is sent to the control module 200.

The screen 210 can then indicate whether or not the applicator 100 has been inserted correctly. When the applicator is not inserted correctly, the control module 200 returns to step E6. Otherwise, in a step E8, the screen 210 invites the user to press on the key 204 in order to start the stimulation program.

Advantageously, a sensitivity test sequence T1 to T4 then begins. This sequence constitutes an original and advantageous characteristic of the invention. It makes it possible not only to begin stimulation at zero intensity while giving a functional role to such stimulation, but it also makes it possible to obtain important medical data, namely the user's sensitivity threshold. A health professional can then measure the effectiveness of the treatment, knowing such data.

In this sequence, in a step T1, the screen 210 invites the user to increase the intensity of stimulation by using the + and − buttons 206 and 207. In another possible embodiment, the increase in intensity may be automatic. During these increments, a step T2 waits for a signal indicating that the button 208 has been pressed.

In application of the instructions for use of the device of the invention, once the patient feels the electrical stimulation, she presses on the button 208. This causes the intensity of the stimulation at that time to be stored. The patient's sensitivity threshold intensity is then accessible to the doctor.

The selected stimulation program is then put into operation in a step T3. The patient then increases the intensity up to an intensity prescribed by the doctor, 30 milliamps (mA) in this example.

While the program is running, the center of the pictogram 215 lights up each time a stimulation starts and turns off when it stops. This enables the user to know when stimulation is taking place in order to contract muscles at the same time. In application of Kegel exercises, such contraction encourages treatment and restoration or reinforcement of muscular structures.

During the treatment, the intensity of the stimulation remains accessible to the user who can modify it as a function of her sensations or of the desired intensity or of the intensity prescribed for the exercise. These modifications are performed using the buttons 206 and 207, e.g. over the range 0 mA to 60 mA.

Stimulation may be stopped at any moment, either by pressing on the button 206 in order to decrease the intensity, or by pressing on the pause button 205, or indeed by pressing on the button 201, thereby stopping stimulation completely.

According to the invention, it is also advantageous for the software managing the operation of the applicator 100 to be such that stimulation is stopped as soon as the sensor 103 detects that the applicator 100 is no longer in contact with the body. This stopping of stimulation may be under the control of the control module 200 to which the signal issued by the sensor 103 is returned, or indeed it may be stopped internally by the applicator itself, with the microprocessor installed therein being suitable for processing the data issued by the sensor 103 and for stopping stimulation.

The duration of stimulation and its intensity are stored automatically in the memory of the control module 200.

Figure 5:
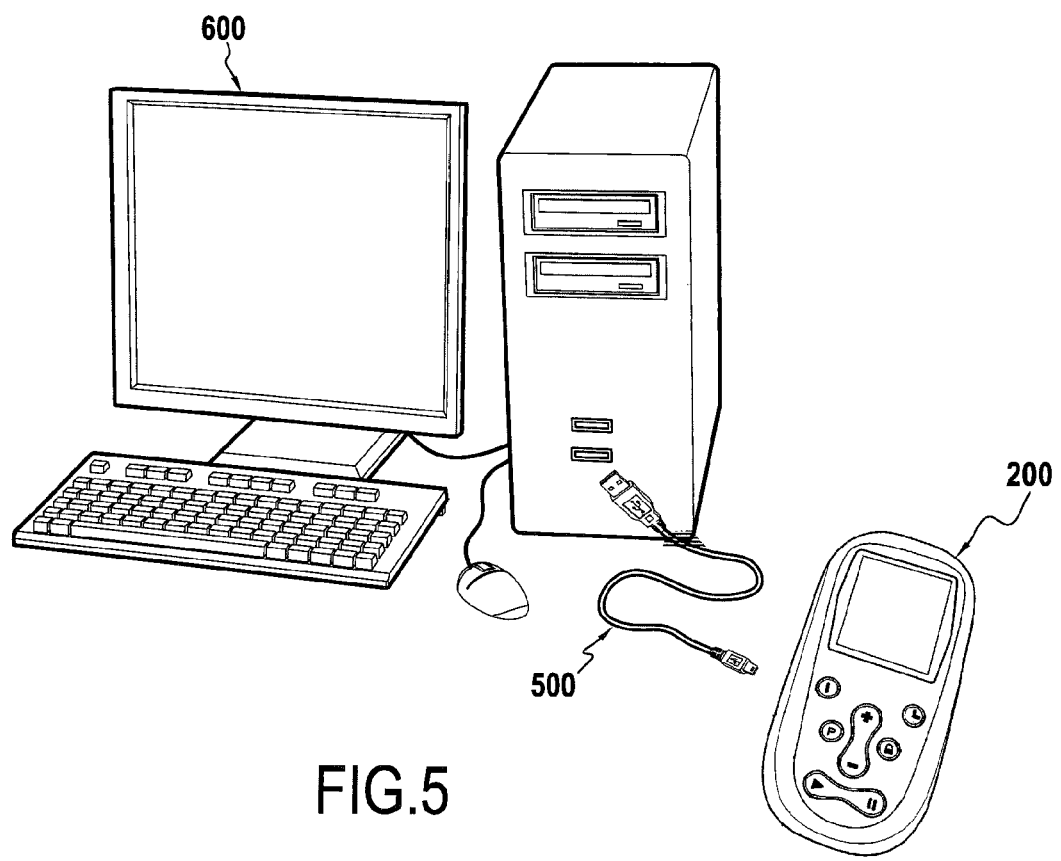
FIG. 5 shows a perineal rehabilitation device of the invention while being connected to a computer.

FIG. 5 shows a stage of connecting the control module 200 to a computer 600. This connection is made via a USB cable 500 having a male USB connector of small size for connecting in the female connector 209 of the control module, and a conventional USB connector suitable for being connected to the computer.

The data stored in the memory of the control module 200 is then accessible to the computer, e.g. to the computer of the attending doctor who prescribes the treatment using the device of the invention.

The stored data preferably relates to the time and date at which a program was applied, the type of program that was selected, the duration of the application, a report on whether the application ran properly (applicator removed during treatment, incomplete duration, in particular), mean applied intensity, and the minimum sensitivity intensity, i.e. the result of the sensitivity test performed at the beginning of application. In the context of biofeedback applications, it is advantageous also to store a so-called "fitness" test showing the automatic adaptation of the intensity of stimulation as a function of progress during the application of the treatment. This provides information about the fatigability of the muscle and about its training.

The "viewing stored data on a computer" mode is advantageously obtained by pressing simultaneously on the button 202 and on the button 204 after the module 200 has been connected to a computer 600. The display of a particular treatment report as selected by the buttons 206 and 207 is obtained by pressing the button 204 on the control module, for example.

It is also possible in the invention to transfer the stored data to the computer 600. Under such circumstances, the data is subsequently presented using a format that is specific to software for reading that data.

Figure 6A:
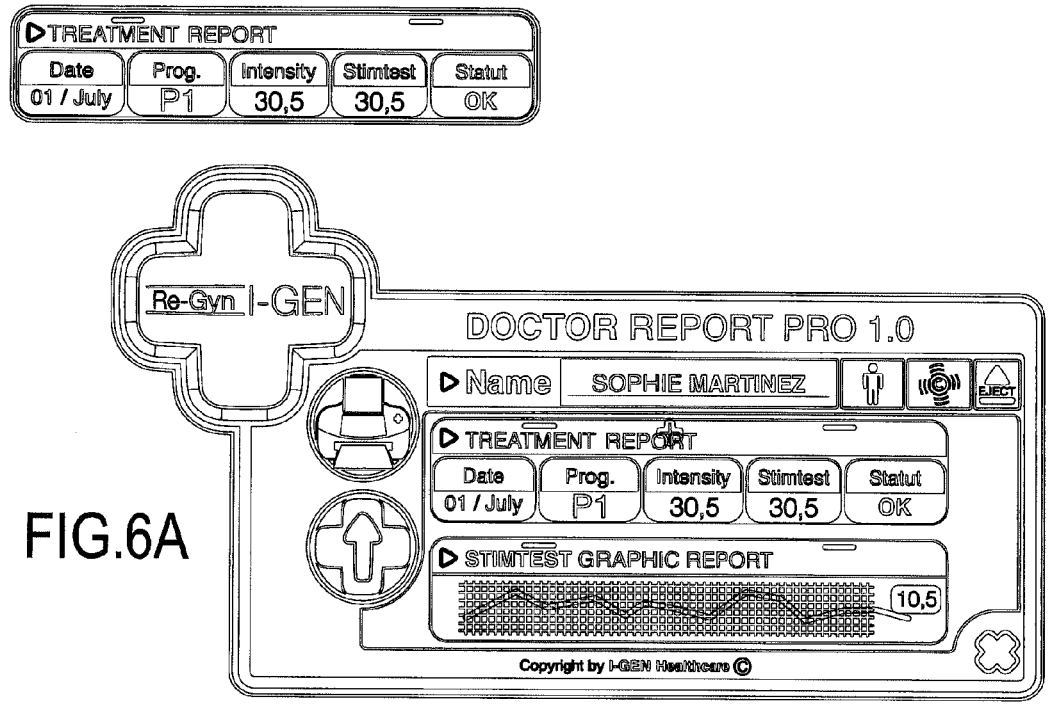
FIG. 6 shows an example of a display on the screen of a computer of data stored in the control module.
Figure 6B:
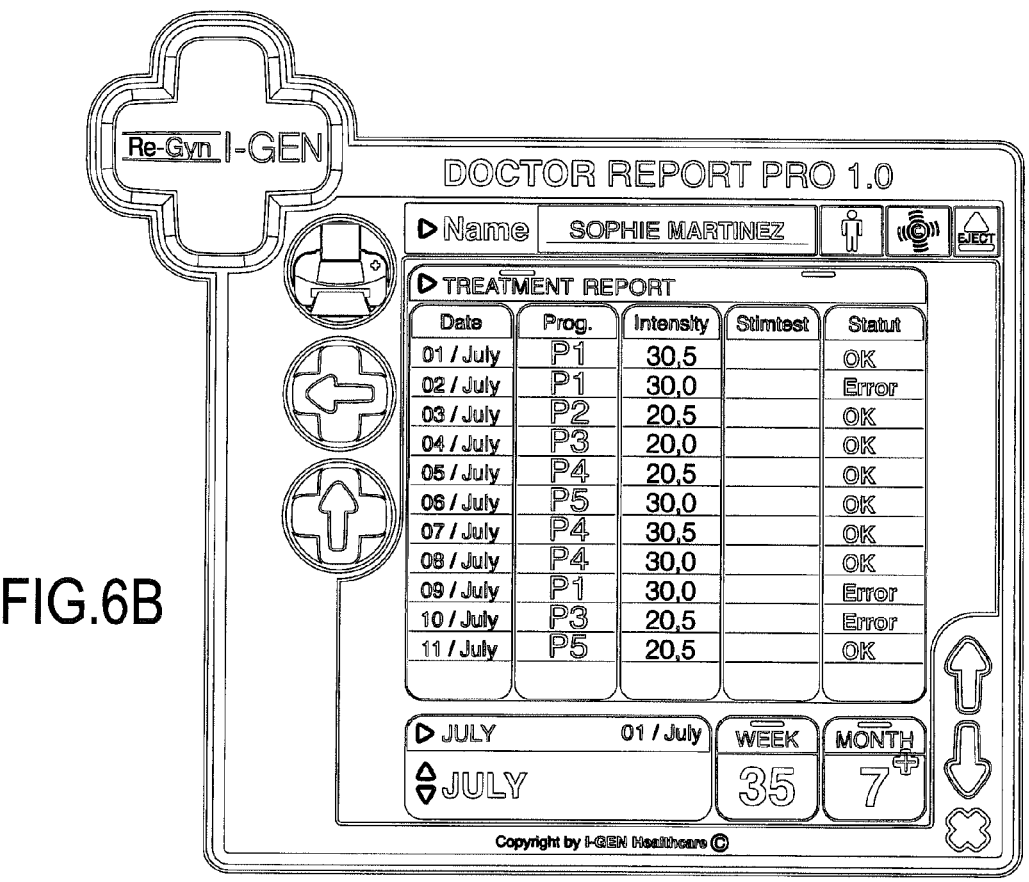

An example of such a display is shown in FIG. 6. In FIG. 6A there can be seen a compact window that shows the first line of a sub-window shown open in FIG. 6B, together with a summary of sensitivity tests.

FIG. 6B shows the list of applications of treatment performed by the patient. The summary of the sensitivity tests in FIG. 6A is in the form of a curve of sensitivity threshold intensities detected by the patient over the set of treatment applications listed in FIG. 6B.

Advantageously, the applicator includes a sensor suitable for measuring the reactions of the patient's body. In an advantageous embodiment, the sensor is a pressure sensor suitable for measuring muscle contraction. By way of example, the sensor may be annular. In particular, it is possible to use a strain gauge type sensor operating in compression.

The measurement of this contraction is then transmitted in real time to the control module 200. The control module has a unit, advantageously a software unit, referred to as a feedback unit and suitable for calculating a modification to the intensity of the stimulation by taking account of the measured muscle contraction.

This characteristic is original and made possible in the invention by the combined use of a bidirectional connection between the wireless applicator and the control module and of a pressure sensor placed directly on the wireless applicator.

Specifically, muscular contraction also weakens after several successive contractions. It then becomes pointless for the muscle that is fatigued or that is becoming fatigued to be stimulated strongly with electricity. This does not enable to work properly. Thus, the invention enables the stimulation to be adapted, while taking account of muscle fatigue, of its magnitude, and of the rate at which it occurs.

Figure 7:
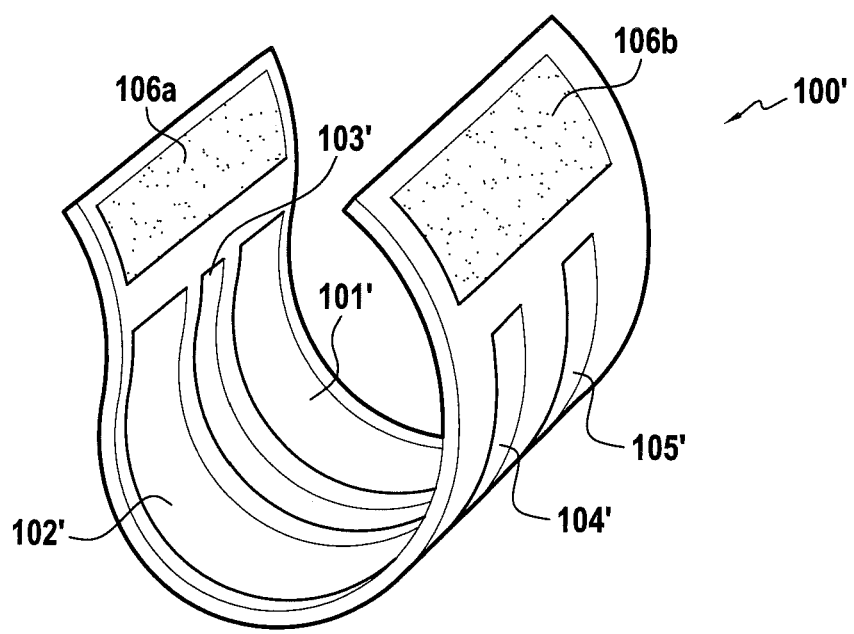
FIG. 7 shows an example of an annular applicator of the arm band type, of the invention.

FIG. 7 shows an annular applicator 100' in the form of an arm band. This applicator 100' is for use in perineal rehabilitation in a man. The band 100' advantageously includes means for imparting an annular shape to the applicator, e.g. strips 106a and 106b of Velcro. This enables the applicator to be put into place so as to surround the erect penis. This applicator is likewise advantageously leaktight.

The applicator 100' include at least one stimulation electrode, here two electrodes 101' and 102', on its inside face, and at least one charging electrode. Here there are two charging electrodes 104' and 105' that are installed on the outside face of the applicator 100'. An electrode 103' is advantageously added to the inside face of the band 100' in order to detect contact with the body.

It should be observed here that the electrodes used are not strictly annular, but form a portion of a circle when the applicator is in its annular configuration, in particular when it is installed. Nevertheless, this does not raise any particular problem for stimulation or for charging.

The charger box for the applicator 100' is advantageously similar in shape to the box 300. A recess for the applicator 100' is likewise formed inside the box. Its shape naturally needs to be adapted to receive the band 100' laid out flat or slightly curved. Advantageously, closing the box presses the band 100' between the two portions of the box so as to ensure contact between the charging electrodes 104' and 105' and contactors of the same type as the contactors 301, 302, and 304 of the box 300.

The operation and control of the applicator 100' is similar to that described for the endocavity applicator 100. The applicator 100' is specifically advantageously controlled with a control module similar to that used with the endocavity applicator 100. Nevertheless, it should be observed that different programs are implemented since the treated dysfunctions may be different. In particular, the rehabilitation device of the invention with an annular applicator may be used for treating certain types of impotence.

Finally, it should be observed that various implementations can be devised on the principles of the invention. In particular, in the absence of a stimulation test, all of the programs could begin by raising intensity progressively and with that rise being stopped by the patient by pressing on a button of the remote control, and with this not involving any storage of the corresponding stimulation intensity.

The invention claimed is:

1. A perineal rehabilitation device comprising an applicator that is an endocavity applicator (100), locally supporting a charging electrode (104, 105) and at least one stimulation electrode (101, 102) on its periphery, and including at least one energy storage unit that is rechargeable via the charging applicator (104, 105), the applicator (100) including at least one microprocessor for executing an electrical stimulation program, the device being characterized in that it further comprises an external control module (200) in the form of a remote control connected to the applicator (100) by a wireless connection and including a user interface for enabling the user to input operating data for the applicator (100) and a control unit for controlling the applicator (100) by sending control signals thereto, the said endocavity applicator comprising:

an oblong portion (100a) designed for insertion into a body cavity, said oblong portion being surrounded with annular electrodes (101-105), an external portion (100b) constituting a handle for removing the applicator after it has been inserted, and the oblong portion (100a) comprising a proximal portion (P) provided with at least two said annular electrodes (101, 102) which are stimulation electrodes to which sequences of electrical stimuli can be applied, and the oblong portion (100a) comprising a distal portion (D) provided with at least the annular electrodes (104, 105) for charging the applicator and said annular electrode (103) for detecting that the applicator has been inserted into the body cavity, the control module (200) capable of:

selecting a treatment program among various predetermined programs (P1-P7) to carry out stimulations with different sequences continuously or during different stimulation times, and selecting the duration of the treatment, and modifying automatically or on user input an intensity of stimulation, and indicating and storing the intensity of stimulation when increasing intensity and that the stimuli begin to be felt by the user, and storing in a memory time-stamped data concerning the operating stimulation intensities and durations ordered to the applicator (100), and stopping the stimulation at any moment.

2. A device according to claim 1, characterized in that all of the programs begin electrical stimulation at zero intensity.

3. A device according to claim 1, characterized in that the control module (200) includes means for indicating stimulation operating ranges of the applicator (100).

4. A device according to claim 1, characterized in that the control module (200) includes at least one connection port (209) for transferring time-stamp data to a computer (600).

5. A device according to claim 1, characterized in that the control module (200) includes means suitable for sending control signals to the applicator (100), causing the applicator to issue automatically stimuli of increasing intensity, and in that the interface includes means enabling the user to indicate the moment when the stimuli begin to be felt.

6. A device according to claim 1, characterized in that the applicator (100) includes means suitable, while the device is in operation, for performing measurements relating to the reaction of the body.

7. A device according to claim 6, characterized in that the applicator (100) includes a pressure sensor for taking measurements relating to muscle contraction.

8. A device according to claim 6, characterized in that the wireless connection is bidirectional and the control module (200) includes a feedback unit for receiving measurements from the applicator, for processing these measurements in real time, for calculating an appropriate operating mode as a function of the measurements, and for sending a control signal corresponding to this mode of operation to the applicator (100).

9. A device according to claim 6, characterized in that the control module (200) includes a memory for storing information relating to the reaction of the body.

10. A device according to claim 1, characterized in that the applicator (100) includes an electrode (103) for detecting that it has been inserted or installed correctly, which electrode is suitable for detecting contact with the body, said electrode (103) being suitable for sending a signal to the microprocessor installed within the applicator and/or the microprocessor installed within the control module, the microprocessor being such as to be suitable for causing stimulation to stop as soon as the applicator is no longer in contact with the body.

11. A device according to claim 1, characterized in that the device enables the rehabilitation treatment of urinary incontinence and said predetermined treatment programs are dedicated to the treatment of various types of incontinency comprising stress incontinence, urge incontinence and mixed incontinence.

* * * * *